(12) United States Patent
Chen et al.

(10) Patent No.: US 11,800,842 B2
(45) Date of Patent: Oct. 31, 2023

(54) **METHOD FOR OBTAINING ADVENTITIOUS TETRAPLOID BUD OF *BLUMEA BALSAMIFERA***

(71) Applicant: Tropical Crops Genetic Resources Institute, Chinese Academy of Tropical Agricultural Sciences, Hainan (CN)

(72) Inventors: Xiaolu Chen, Haikou (CN); Fulai Yu, Haikou (CN); Yongfeng Xiao, Haikou (CN); Yulan Li, Haikou (CN); Qin Luo, Haikou (CN); Ping Yu, Haikou (CN); Yinghua Chen, Haikou (CN); Yong Yang, Haikou (CN); Kai Wang, Haikou (CN); Chao Yuan, Haikou (CN); Dan Wang, Haikou (CN); Lingliang Guan, Haikou (CN); Yingbo Zhang, Haikou (CN); Mei Huang, Haikou (CN); Xiaoli Xie, Haikou (CN); Zhenxia Chen, Haikou (CN)

(73) Assignee: TROPICAL CROPS GENETIC RESOURCES INSTITUTE, CHINESE ACADEMY OF TROPICAL AGRICULTURAL SCIENCES, Haikou (CN)

( * ) Notice: Subject to any disclaimer, the term of this patent is extended or adjusted under 35 U.S.C. 154(b) by 0 days.

(21) Appl. No.: 18/079,850

(22) Filed: Dec. 12, 2022

(65) Prior Publication Data
US 2023/0180689 A1    Jun. 15, 2023

(30) Foreign Application Priority Data
Dec. 14, 2021    (CN) .......................... 202111522569.0

(51) Int. Cl.
*A01H 1/08*    (2006.01)
*A01H 4/00*    (2006.01)

(52) U.S. Cl.
CPC .............. *A01H 1/08* (2013.01); *A01H 4/002* (2021.01)

(58) Field of Classification Search
CPC ........................................................ A01H 1/08
USPC ........................................................... 435/410
See application file for complete search history.

(56) References Cited

FOREIGN PATENT DOCUMENTS

| CN | 103688856 A |   | 4/2014 |
| CN | 105309315   | * | 2/2016 |
| CN | 105309315 A |   | 2/2016 |
| CN | 111296286   | * | 6/2020 |
| CN | 114391474 B |   | 11/2022 |

OTHER PUBLICATIONS

Nilanthi et al. Journal of Biomedicine and Biotechnology 2009:1-7 (Year: 2009).*
First office action dated Sep. 1, 2022, in related Chinese Patent Appl. No. 202111522569.0, 7 pages.

* cited by examiner

*Primary Examiner* — Li Zheng
(74) *Attorney, Agent, or Firm* — Bochner PLLC; Andrew D. Bochner

(57) ABSTRACT

The present disclosure provides a method for obtaining adventitious tetraploid buds of *Blumea balsamifera*, comprising the following steps: selecting a root segment of diploid *B. balsamifera* as an explant, culturing the root segment in a chromosome doubling inducing medium supplemented with 0.025-0.1 mg/L 1-naphthaleneacetic acid (NAA), 1.0-2.0 mg/L 6-benzylaminopurine (6-BA), and 90-150 mg/L colchicine, inducing explant cells, and simultaneously doubling chromosomes and differentiating the adventitious buds. The present disclosure fills the blank of using a root of *B. balsamifera* as the explant and increases effective explant sources during the propagation, proliferation and biotechnological breeding of *B. balsamifera*. More importantly, root cells of the *B. balsamifera* are directly differentiated into adventitious buds while chromosomes are doubled, and a callus formation process is not needed, so that the technical links are simplified and the variation of regeneration buds and the generation of chimeras are reduced.

4 Claims, 2 Drawing Sheets

METHOD FOR OBTAINING ADVENTITIOUS TETRAPLOID BUD OF *BLUMEA BALSAMIFERA*

CROSS REFERENCE TO RELATED APPLICATION

This patent application claims the benefit and priority of Chinese Patent Application No. 202111522569.0, filed with the China National Intellectual Property Administration on Dec. 14, 2021, the disclosure of which is incorporated by reference herein in its entirety as part of the present application.

TECHNICAL FIELD

The present disclosure belongs to the technical field of plant polyploid breeding, and in particular relates to a method for obtaining adventitious tetraploid buds of *Blumea balsamifera*.

BACKGROUND

*Blumea balsamifera* (L.) DC. is a perennial herb of the genus *Blumea* of the family Asteraceae and distributes in Yunnan, Guizhou, Hainan, and Taiwan, China. It is the only source of traditional Chinese medicine *Blumea* camphor (L-borneol). *B. balsamifera* extract is the main raw material of a plurality of Chinese patent medicines, and is widely used in food, cosmeceuticals and other market fields, with excellent market prospects.

For a long time, the cultivation techniques of *B. balsamifera* are relatively backward, and the difficulty of propagation of elite seedlings is the main problem. The production of *B. balsamifera* has been mainly based on cultivation of seedlings and root-cuttings. Seed propagation (seedling cultivation) belongs to sexual propagation. The disadvantage thereof is that the germination rate of seeds is low, and the traits of the progenies are different. Because of this, the stock traits cannot be maintained by seed propagation in *B. balsamifera*. Root propagation (cultivation of root-cuttings) belongs to asexual propagation, and the disadvantage is that the pathogens of the stock plants cannot be excluded and the efficiency is also low. Therefore, it is necessary to carry out the in vitro propagation study of *B. balsamifera* seedlings. *B. balsamifera* is a medicinal plant, and its medicinal component, L-borneol, belongs to a secondary metabolite of *B. balsamifera*. Polyploid breeding is theoretically beneficial to promote the accumulation of secondary metabolites of *B. balsamifera*, including L-borneol. Therefore, polyploid breeding is an important strategy for biological technology breeding of *B. balsamifera*.

Many previous attempts to *B. balsamifera* chromosome doubling technology were mainly based on the induction of chromosome doubling in axillary buds. However, these techniques have fundamental flaws. Induction of axillary bud proliferation is the most commonly used technique for rapid propagation of *B. balsamifera* seedlings, which stimulates the growth of the original lateral bud growing points of the plant, and does not involve the process of cell dedifferentiation. If artificial mutagenesis or transgenesis is attempted in this way, the chance of obtaining chimeras will be high, because it is difficult to mutate or transform all the diploid cells that make up the original bud, and these two kinds of cells will mix together, resulting in the formation of chimeras. During the growth of a chimera, the ratio of the two kinds of cells will change, with the mutaged or transformed cells become less and less, leading to the failure of breeding efforts.

In the prior art, axillary buds composed of differentiated cells are treated. Because in the process of artificially inducing chromosome doubling, only cells that are undergoing mitosis can be induce to double the chromosomes, incomplete treatment may be mostly caused, and only partial cells in a bud can be induced to double the chromosomes. Since the buds obtained by the above way have both doubled cells (tetraploid) and undoubled cells (diploid), these buds are chimeras. As mentioned before, chimeras are unstable, and because of this, the prior art is difficult to meet the breeding needs of *B. balsamifera*.

Another possible technique is the use of leaf explants. In this method, diploid calluses are induced form diploid leaf explants with a culture medium, and then diploid calluses are artificially induced to double the chromosomes into tetraploid calluses. The tetraploid calluses are then transferred to another culture medium to form tetraploid adventitious buds. However, successful cases of application of this technology in the polyploid breeding of *B. balsamifera* have not been documented yet. Usually, artificial mutagenesis is carried out at the callus stage, but because it is very difficult to mutate all the cells in a callus, most possibly non-mutated cells may together with mutated cells to form adventitious chimera buds. In addition, this technique needs to go through three steps: preparing at least three culture media, inoculating at least three times for three different stages. Therefore, not only is the process cumbersome, but also leads to certain probability of unintended mutation occurring at the callus stage, thereby interfering with mutagenesis or genetic transformation results.

In view of this, there is still a lack of a tissue culture method that does not produce chimeras or has a low chimera rate, more reliable to obtain adventitious tetraploid buds of *B. balsamifera*.

SUMMARY

Stem segments with buds (apical and axillary buds) of diploid plants are only adopted as explants in the existing *B. balsamifera* polyploid technology and tetraploids are induced by stimulating pre-existing buds (apical and axillary buds). To overcome the deficiency, an objective of the present disclosure is to provide a method for inducing the simultaneous doubling and direct differentiation of root cells to produce adventitious buds by using roots of diploid *B. balsamifera* as explant material. The present disclosure does not require the explants to have pre-existing definite buds (terminal or axillary buds), but directly doubles the chromosomes of the somatic cells and then induces the differentiation of the cells into adventitious buds. The advantage of the present disclosure is that each cell can form a bud independently and directly, without producing a large number of chimeras mixed with heterogeneous cells, thereby improving the accuracy of site-directed mutagenesis or genetic transformation. The present disclosure not only establishes a technical foundation for obtaining complete tetraploids, but also provides technical reference for the artificial mutagenesis and transgenosis of *B. balsamifera*.

A first objective of the present disclosure is to provide a method for simultaneously doubling the chromosomes in diploid *B. balsamifera* somatic cells, and to induce the chromosome-doubled cells to differentiate directly into adventitious tetraploid buds.

A second objective of the present disclosure is to provide a method of using diploid *B. balsamifera* root tissues for directly differentiating the root cells into adventitious tetraploid buds without a callus stage.

To achieve the above objectives, the present disclosure is achieved through the following solution:

The present disclosure claims a method for obtaining tetraploid adventitious buds using root explants of diploid *B. balsamifera*. The regenerated adventitious tetraploid buds obtained is derived from root-explants of diploid *B. balsamifera*; By the method, tetraploid buds can be obtained by preparing only once the culture medium and once inoculation of the root-explants.

The method includes the following steps: selecting healthy roots of in vitro diploid *B. balsamifera* plantlets, cutting the roots into segments as explants, and culturing the explants on a chromosome doubling inducing medium supplemented with 0.025-0.1 mg/L 1-naphthaleneacetic acid (NAA), 1.0-2.0 mg/L 6-benzylaminopurine (6-BA), and 90-150 mg/L colchicine.

Preferably, the chromosome doubling inducing medium may be a basal medium supplemented with 0.025-0.1 mg/L NAA, 1.0-2.0 mg/L 6-BA, 90-150 mg/L colchicine, 10-70 g/L sucrose, and 2-8 g/L agar.

Preferably, the roots may be normal roots or adventitious roots.

Preferably, culturing time may be 20-60 days.

Preferably, after the roots are cut into segments, a root segment may be greater than 2 cm in length.

More preferably, after the roots are cut into the segments, the root segment may be 4-8 cm in length. If the length is shorter, the efficiency of inducing the adventitious buds may be low. If the length is longer, the efficiency of inducing the adventitious buds may be high. However, if the length is too long, the number of explants that can be obtained from the same number of roots is too small.

Preferably, the basal medium may be ½ MS Medium or MS Medium.

More preferably, the chromosome doubling inducing medium may be a basal medium supplemented with 0.05 mg/L NAA, 1.0 mg/L 6-BA, 120 mg/L colchicine, 30 g/L sucrose, and 6 g/L agar.

Compared with the prior art, the present disclosure has the following beneficial effects:

(1) The present disclosure overcomes the deficiency that only stem segments with buds are previously selected as explants for proliferation and induced doubling of definite buds (apical and axillary buds), and provides a method for using a root of *B. balsamifera* as an explant material to induce direct doubling of root cells in one step and simultaneously differentiate into adventitious tetraploid buds. The present disclosure fills in the blank of the root of *B. balsamifera* as an explant material for polyploid breeding of *B. balsamifera*. The application results of the present disclosure show that the root of *B. balsamifera* can not only be used as an explant for proliferation and doubling, but even as a better option for explant selection. The use of the root explant increases the object of culturable explant material, namely, an effective source of explants for *B. balsamifera* in the process of biotechnological breeding.

(2) Diploid *B. balsamifera* root cells can be used for direct doubling and simultaneous differentiation into adventitious tetraploid buds. The method is simpler and faster than the prior art, and reduces the generation of chimeras.

(3) The present disclosure saves consumables, time, and labor cost, improves the accuracy of site-directed mutagenesis or genetic transformation of *B. balsamifera*, and provides a technical basis for artificial mutagenesis and cell engineering breeding of *B. balsamifera*.

DETAILED DESCRIPTION OF THE EMBODIMENTS

Figure 1:
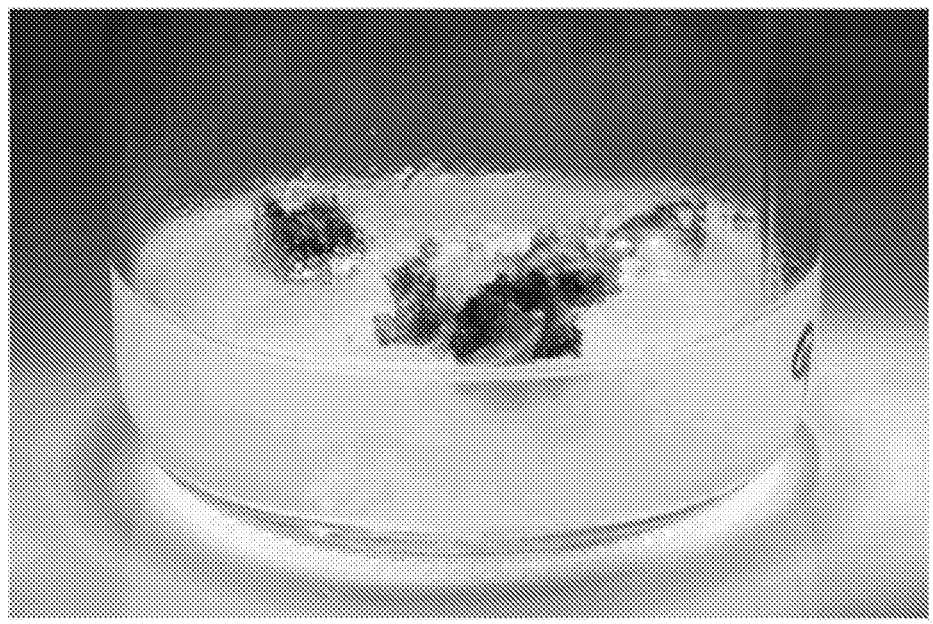
FIG. 1 illustrates an effect of adventitious tetraploid buds of *B. balsamifera* induced by explants of *B. balsamifera*.
Figure 2:
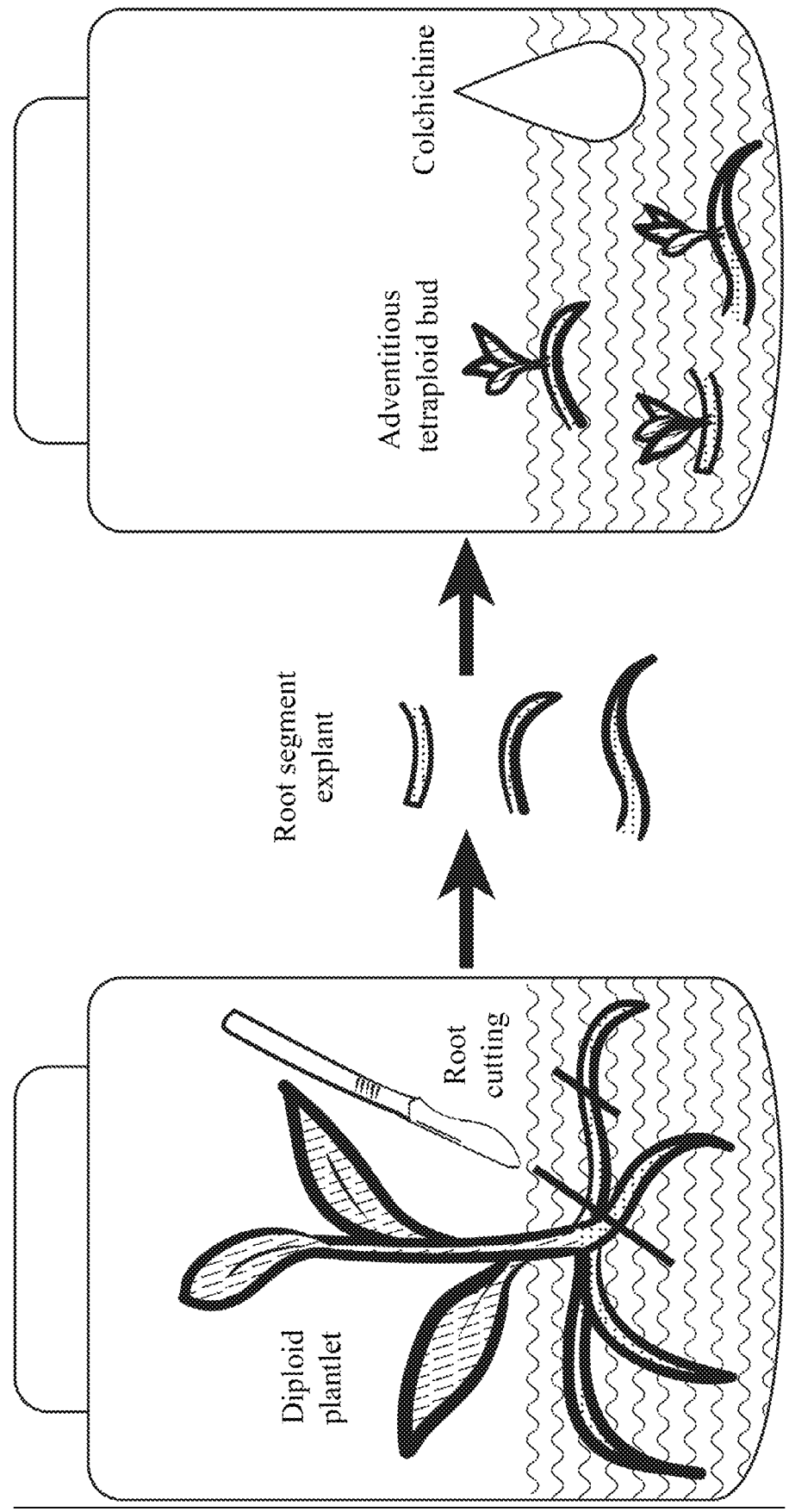
FIG. 2 schematically illustrates operations of induction of adventitious tetraploid buds of *B. balsamifera* by explants of *B. balsamifera*.

In order to better understand the technical content of the present disclosure, specific examples will be provided below to further illustrate the present disclosure. The test methods used in the following examples are conventional methods unless otherwise specified; the materials and reagents used are commercially available reagents and materials unless otherwise specified.

All sterile seedlings used in the present disclosure were derived from *B. balsamifera* tissue cultured plantlets cultivated in the South China Medicinal Plant Tissue Culture Room, Tropical Crops Genetic Resources Institute, Chinese Academy of Tropical Agricultural Sciences, Danzhou City, Hainan Province from September 2019 to October 2020.

In the examples, effective root segment refers to uncontaminated root segment; induction rate refers to the percentage of the total number of adventitious tetraploid buds formed by induction accounting for the total number of diploid explants, and the calculation formula is: induction rate (%)=(total number of adventitious tetraploid buds/total number of diploid explants)×100%. Chimera rate (%)=(total number of adventitious buds of chimera/total number of adventitious buds)×100%.

Example 1 A Method for Obtaining Adventitious Tetraploid Buds of *B. balsamifera*

Step S1. Healthy *B. balsamifera* seeds were routinely sterilized, sown in a sterile manner, and cultivated for 12 days to obtain sterile *B. balsamifera* seedlings, and their root tissues were collected.

Step S2. The obtained root tissues were segmented, and the root segments were 1-8 cm in length.

Step S3. Segmented root tissues were cultivated in chromosome doubling inducing medium for 20 days to obtain adventitious buds.

Herein, the sterile seeding medium was based on ½MS Medium, which was further supplemented with 0.01-0.5 mg/L NAA, 20-50 g/L sucrose, and 3-7 g/L agar.

The chromosome doubling inducing medium was based on MS Medium, which was supplemented with 0.05 mg/L NAA, 0.1 mg/L 6-BA, 120 mg/L colchicine, 30 g/L sucrose, and 6 g/L agar.

Step S4. Chromosome ploidy identification was conducted on the obtained adventitious buds, the number of tetraploid buds was counted, and the induction rate of tetraploid buds was calculated.

The results showed that tetraploid buds were hardly obtained when the diploid root segments were 1-2 cm in length. Therefore, if the root segment is divided into 1-2 cm in length according to the routine operation and cultured on the chromosome doubling inducing medium, it will not be possible to achieve the objective of doubling and obtain polyploid plants. Only when the length of the diploid root segment reaches or exceeds 4 cm, the doubled adventitious tetraploid buds can be obtained.

TABLE 1

| Length of diploid root segment (cm) | Number of diploid explants | Number of tetraploid buds | Induction rate of tetraploid buds (%) |
|---|---|---|---|
| 1 | 96 | 0 | 0 |
| 2 | 96 | 1 | 1.04 |
| 4 | 96 | 11 | 11.46 |
| 8 | 96 | 12 | 12.50 |

Example 2 A Method for Obtaining Adventitious Tetraploid Buds of *B. balsamifera*

Step S1. Explants were cultivated in adventitious root induction medium to differentiate to obtain adventitious roots, and explants were cultivated for 30 days.

Step S2. The adventitious roots were cut into segments, and each segment was 6 cm in length.

Step S3. Stem segments with buds were cultivated by conventional *B. balsamifera* tissue culture technology, each stem segment with buds was 2-3 cm in length, and each stem segment had 2-3 in vivo apical or axillary buds.

Step S4. Segmented adventitious roots and stem segments with buds were cultivated in chromosome doubling inducing medium for 60 days to obtain adventitious buds.

Herein, the adventitious root induction medium was based on ½MS Medium, which was further supplemented with 0.01-0.5 mg/L NAA, 20-50 g/L sucrose, and 3-7 g/L agar.

The chromosome doubling inducing medium was based on ½MS Medium, which was further supplemented with 0.1 mg/L NAA, 2.0 mg/L 6-BA, 120 mg/L colchicine, 70 g/L sucrose, and 6 g/L agar.

Step S5. Chromosome ploidy identification was conducted on the obtained adventitious buds, the numbers of diploid, tetraploid, and chimeric buds were counted, and the induction rate of tetraploid buds and the chimera rate were calculated.

The results show that the technology of obtaining tetraploids by induced doubling with roots as explants has higher efficiency of adventitious buds and a lower chimera rate compared with the prior art.

TABLE 2

| Type of explant | Number of explants | Induction rate of tetraploid buds (%) | Chimera rate (%) |
|---|---|---|---|
| Root segment | 96 | 10.42 | 30.00 |
| Stem segment with buds | 96 | 6.25 | 83.33 |

Example 3 Effects of Different BA Concentrations

I. Experimental Method

MS Medium was used as a basal medium, which was supplemented with 0.05 mg/L NAA, 120 mg/L colchicine, 30 g/L sucrose, 6 g/L agar, and 6-BA of different concentrations (0, 1.0, 1.5, and 2.0 mg/L, respectively, 0 mg/L as the control group). Culture media were prepared individually, segmented root tissues (with a root segment length of about 6.0 cm) were inoculated, and contaminated root explants were excluded after 60 days. The number of tetraploid buds was counted, and the doubling efficiency was calculated.

II. Experimental Results

The results are shown in Table 3. When the concentration of 6-BA added in the culture medium was 1.0 mg/L, the effect of inducing the doubling of the somatic cells of the root explants of *B. balsamifera* and dedifferentiating into adventitious tetraploid buds was optimal.

TABLE 3

Effects of different 6-BA concentrations on adventitious buds formed by dedifferentiation of *B. balsamifera* somatic cells

| 6-BA concentration (mg/L) | Induction rate (%) |
|---|---|
| 0 | 0 |
| 1.0 | 7.75 |
| 1.5 | 5.5 |
| 2.0 | 4.17 |

Example 4 Effects of Different NAA Concentrations

I. Experimental Method

MS Medium was used as a basal medium, which was supplemented with 1.0 mg/L 6-BA, 120 mg/L colchicine, 30 g/L sucrose, 6 g/L agar, and NAA of different concentrations (0, 0.025, 0.05, 0.075, and 0.1 mg/L, respectively, 0 mg/L as the control group). Culture media were prepared individually, and segmented root tissues (with a root segment length of about 4.0 cm) were inoculated. Chromosome ploidy identification was conducted on adventitious buds after 60 days. The number of adventitious tetraploid buds was counted, and the induction rate was calculated.

II. Experimental Results

The results showed that the doubling effect was optimal when the NAA concentration was 0.05 mg/L.

TABLE 4

Effects of different NAA concentrations

| NAA concentration (mg/L) | Induction rate % |
|---|---|
| 0 | 0 |
| 0.025 | 2.08 |
| 0.05 | 10.42 |
| 0.075 | 4.17 |
| 0.1 | 3.13 |

Example 5 Effects of Different Colchicine Concentrations

I. Experimental Method

MS Medium was used as a basal medium, which was supplemented with 1.0 mg/L 6-BA, 0.05 mg/L NAA, 30 g/L sucrose, 6 g/L agar, and colchicine of different concentrations (50, 70, 90, 120, and 150 mg/L, respectively). Culture media were prepared individually, and segmented root tissues (with a root segment length of about 4.0 cm) were inoculated. Chromosome ploidy identification was conducted on the formed adventitious buds after 60 days. The number of adventitious tetraploid buds was counted, and the doubling induction rate was calculated.

II. Experimental Results

The results showed that the effect of inducing root explants of diploid *B. balsamifera* to form adventitious tetraploid buds was optimal when the colchicine concentration was 120 mg/L.

TABLE 6

Effects of different colchicine concentrations on adventitious buds formed by dedifferentiation of *B. balsamifera* somatic cells

| Colchicine concentration (mg/L) | Induction rate % |
|---|---|
| 50 | 0 |
| 70 | 0 |
| 90 | 2.08 |
| 120 | 10.42 |
| 150 | 4.17 |

The above descriptions are only preferred examples of the present disclosure and are not intended to limit the present disclosure. Any modifications, equivalent substitutions and improvements made within the spirit and principles of the present disclosure shall be included in the protection scope of the present disclosure.

What is claimed is:

1. A method for obtaining adventitious tetraploid buds of *Blumea balsamifera*, comprising the following steps: selecting healthy roots of in vitro diploid *Blumea balsamifera* plantlets, cutting the roots into segments with a root segment length of 4-8 cm as explants, and culturing the explants on a chromosome doubling inducing medium supplemented with 0.025-0.1 mg/L 1-naphthaleneacetic acid (NAA), 1.0-2.0 mg/L 6-benzylaminopurine (6-BA), and 90-150 mg/L colchicine; wherein the chromosome doubling inducing medium is a basal medium supplemented with 0.025-0.1 mg/L NAA, 1.0-2.0 mg/L 6-BA, 90-150 mg/L colchicine, 10-70 g/L sucrose, and 2-8 g/L agar; and the basal medium is ½ MS Medium or MS Medium.

2. The method for obtaining adventitious tetraploid buds of *Blumea balsamifera* according to claim 1, wherein the roots comprises normal roots.

3. The method for obtaining adventitious tetraploid buds of *Blumea balsamifera* according to claim 1, wherein the culturing lasts for 20-60 days.

4. The method for obtaining adventitious tetraploid buds of *Blumea balsamifera* according to claim 1, wherein the chromosome doubling inducing medium is a basal medium supplemented with 0.05 mg/L NAA, 1.0 mg/L 6-BA, 120 mg/L colchicine, 30 g/L sucrose, and 6 g/L agar.

* * * * *